United States Patent [19]

Permér

[11] Patent Number: 4,660,424
[45] Date of Patent: Apr. 28, 1987

[54] METERING VALVE

[75] Inventor: Christer Permér, Huddinge, Sweden

[73] Assignee: Lars Ljungberg, Lab Trade AB, Stockholm, Sweden

[21] Appl. No.: 793,766

[22] Filed: Nov. 1, 1985

[30] Foreign Application Priority Data

Nov. 6, 1984 [SE] Sweden ................................. 8405561

[51] Int. Cl.$^4$ ............................................. G01N 1/00
[52] U.S. Cl. .................................................... 73/864.83
[58] Field of Search ........... 73/864.81, 864.83, 864.84, 73/864.85, 864.91, 864, 864.31, 864.33, 864.34; 137/597, 625.2, 625.47

[56] References Cited

U.S. PATENT DOCUMENTS

| 3,475,950 | 11/1969 | Ferrin | 73/864.83 |
| 4,059,009 | 11/1977 | Ball et al. | 73/864.83 |
| 4,152,391 | 5/1979 | Cabrera | 73/864.83 |
| 4,411,575 | 10/1983 | Miller | 73/864.81 |
| 4,476,731 | 10/1984 | Charney et al. | 73/864.83 |

FOREIGN PATENT DOCUMENTS

| 0855234 | 11/1960 | United Kingdom | 73/864.83 |
| 0603900 | 4/1978 | U.S.S.R. | 73/864.83 |

OTHER PUBLICATIONS

Alperstein, "A Gas Sampling and Injection Valve for Vacuum Service", Analytical Chemistry, 1966, p. 366.

Primary Examiner—Stewart J. Levy
Assistant Examiner—Robert R. Raevis
Attorney, Agent, or Firm—Nies, Webner, Kurz & Bergert

[57] ABSTRACT

A metering valve for extracting a given volume of fluid from a first fluid flow and introducing the thus extracted volume of fluid to a second fluid flow, comprising a stationary valve component provided with a first and a second supply channel and a first and a second discharge channel, and a metering component which can be rotated relative to the stationary valve component and which incorporates a metering channel of the aforementioned given volume. In accordance with the invention, the valve component (2) has a planar surface (9) into which the aforementioned supply and discharge channels open out. The metering component (7) also includes a planar surface (10) which abuts against the planar surface (9) of the valve component (2) and into which the two ends of the metering channel open out. These ends are so located that in the first position of rotation of the metering component (7) in relation to the valve component (2) they connect the first supply channel with the first discharge channel of the valve component (2) and in a second position of rotation connect the second channels of the valve component (2).

9 Claims, 7 Drawing Figures

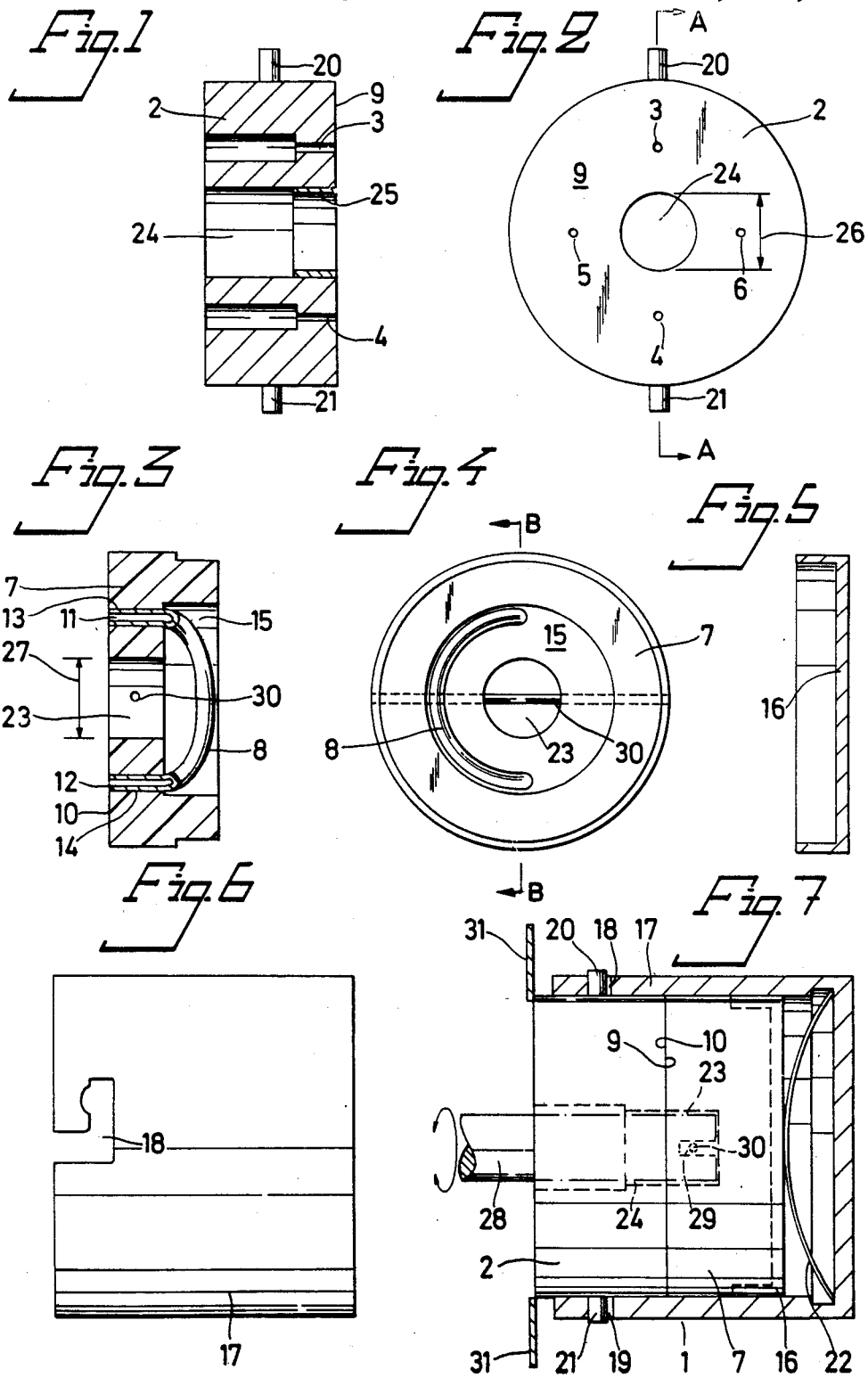

METERING VALVE

The present invention relates to a metering valve for extracting a given minor quantity of fluid to be mixed with a larger quantity of another fluid.

More specifically the invention relates to a metering valve for use in diluting apparatus, in which a small volume of blood is mixed with a large quantity of a diluting fluid and the resultant mixture subsequently analyzed. This analysis may comprise, for example, counting the number of blood corpuscles present, in which case the mixture is passed through a blood counter.

Various diluting apparatus provided with valves which enable a given quantity of blood to be extracted are known to the art. A number of these known apparatus comprise a stationary housing incorporating a plurality of channels, and a member which can be rotated in the housing and which presents a radially through-passing channel which can be caused to connect up pairs of channels located in the housing, by appropriate rotation of the member therein. This enables blood to be pumped into the channel located in the rotatable member, by connecting up a pair of channels in the housing through which blood is pumped. The member is then rotated, so as to extract from said blood through-flow a precise amount of blood corresponding to the volume of the channel in the rotatable member. The channel located in the rotatable member may be turned to a further position in which it connects up a pair of channels intended for the transportation of diluting fluid. When diluting fluid is transported and the rotatable member occupies its latter position of rotation, the extracted quantity of blood is carried away with the diluting liquid.

Such apparatus are primarily encumbered with two drawbacks.

The first of these drawbacks is that blood or other body fluids tend to escape in minute quantities through the gap present between the rotatable member and the stationary housing. Despite the fact that only minute quantities of fluid escape, it is nevertheless necessary to clean the outer surfaces of the rotatable member and the corresponding inner surfaces of the housing from time to time, in order to prevent subsequent samples being contaminated with residual matter from preceding samples. The particular construction of known apparatus renders it necessary to dismantle the valve in order to clean the aforesaid surfaces, which is time consuming and often difficult.

The other drawback is that the valve is constructed to extract solely a given volume of, for example, blood. It is often desirable, however, to extract larger or smaller volumes of blood. It is necessary in known apparatus of this kind to replace the existing valve with a valve of different volume appropriate to the volume of fluid to be extracted.

Furthermore, so-called double-dilution processes are often carried out, in which, for example, 20 microliters of blood are extracted and mixed, for example, with 10 milliliters of diluting liquid to provide a diluted mixture of liquids. A sample volume of, for example, 30 microliters is then taken from the diluted mixture of liquids and mixed in turn with 10 milliliters of diluting liquid, and the resultant final double diluted mixture then analyzed.

Apparatus for carrying out such double-diluting processes are known to the art, in which known apparatus the rotatable member of one and the same valve is provided with a plurality of diametrically arranged channels of mutually different volume.

Because such valves are more complex, the task of dismantling and cleaning the same is still more time consuming. The use of such double-dilution valves also means that valves must be provided for each degree of double-dilution.

The present invention fully eliminates these drawbacks. A metering valve according to the invention can be dismantled for cleaning purposes both quickly and without difficulty, and is constructed to enable a change in the volume of fluid to be extracted to be effected rapidly and with ease.

Thus, the present invention relates to a metering valve which is adapted to extract a given volume of fluid from a first flow and to pass a thus extracted volume to a second flow; and which includes a stationary valve component provided with a first and a second supply channel and a first and a second discharge channel; and a metering component which can be rotated relative to the stationary component and which incorporates a metering channel having the aforesaid given volume, the valve being characterized in that the valve component has a planar surface into which said supply and discharge channels open out; and in that the metering component includes a planar surface which abuts the planar surface of the valve component and into which both ends of the metering channel open out, these channel ends being positioned so that in a first position of rotation of the metering component relative to the valve component said ends connect the first supply channel with the first discharge channel of the valve component, and in a further position of rotation connect up the second channels of the valve component.

An exemplary embodiment of the invention will now be described in more detail with reference to the accompanying drawing, in which FIG. 1 is a cross-sectional view of a valve component taken on the line A—A in FIG. 2;

FIG. 2 is a side view of the valve component, seen from the right in FIG. 1;

FIG. 3 is a cross-sectional view of a metering component taken on the line B—B in FIG. 4;

FIG. 4 is a side view of the component shown in FIG. 3;

FIG. 5 is a cross-sectional view of a lid;

FIG. 6 is a side view of a sleeve; and

FIG. 7 is a side view of an assembled valve component, metering component and sleeve, the sleeve being shown in section.

A metering valve of the illustrated kind is intended to be connected to a diluting apparatus incorporating pumps, in the illustrated embodiment electronic circuits for controlling rotary movement of the metering valve or valves with the aid of electric motors, diluting-fluid containers, suction lines for removing samples fluid, such as blood etc., by suction. Since the diluting apparatus per se forms no part of the present invention it will not be described in detail.

FIGS. 1–6 illustrate various components of a metering valve according to the invention. The metering valve 1, see FIG. 7, is intended to extract a given volume of fluid from a first fluid flow, for example blood extracted by suction through a test tube, and to then pass the extracted volume of fluid to a further fluid flow, for example a diluting fluid which is withdrawn by suction in a given quantity which is much greater than the volume of fluid extracted from the first flow.

The metering valve includes a stationary valve component 2, see FIGS. 1 and 2, which is provided with a first supply channel 3 and a first discharge channel 4, and a second supply channel 5.and a second discharge channel 6. The metering valve also incorporates a metering component 7 which can be rotated in relation to the stationary valve component and which is provided with a metering channel 8 having the aforesaid given volume, see FIGS. 3 and 4. FIG. 4 illustrates the metering channel 8 turned on one side for the sake of clarity. The valve component 2 has a planar surface 9 in which channels 3-6 open out. The metering component 7 also has a planar surface 10 in which the two ends 11,12 of the metering channel 8 open out. When the valve is assembled, the planar surface 10 of the metering component 7 lies against the planar surface of the valve component 2, see FIG. 7.

The ends 11,12 of the metering channel 8 are positioned so that in a first position of rotation of the metering component 7 relative to the valve component 2, the first supply channel 3 is connected to the first discharge channel 4 of the valve component 2, and so that in a second position of rotation of the metering component 7 in relation to the valve component 2, the metering channel connects the second supply channel 5 to the second discharge channel 6 of the valve component 2.

In the first position of rotation of the metering component the said first channels 3,4 are able to connect, for example, a suction line in a test tube containing blood with a suction pump. In the second position of rotation of the metering component the said second channels are able to connect a vessel containing diluting fluid with a discharge line which opens into a collecting vessel for receiving diluted blood. As illustrated by way of example in FIG. 2, the two rotational positions of the metering component may be displaced through 90° in relation to one another.

The whole of the metering channel 8 may comprise a hose, preferably made of a plastics material. The ends 11, 12 of the hose 8 are inserted into axially directed holes 13,14 in the metering component 7, these holes opening into the planar surface 10. The volume to be extracted by the metering component 7 is varied primarily by varying the length of the hose 8 and secondly its inner diameter. The holes 13,14 of all metering components are suitably of mutually the same diameter, said metering components being intended to co-act, one by one, with one and the same valve component.

It will be understood that the aforesaid given fluid volume is adapted for the particular use in question. Volumes of from 10-250 microliters are normal.

A concentrically located chamber 15 is provided in the metering component 7 on the opposite side of the planar surface. This chamber 15 is intended to accommodate the hose 8. As shown in FIG. 5, the chamber or space 15 is sealingly closed by a lid 16, which is placed on the metering component 7, see FIG. 7. This prevents contaminants from entering the metering component. When the lid is applied it also lies against the hose 8, thereby rendering movement of the ends 11,12 of the hose 8 relative to the planar surface 10 difficult.

In accordance with one preferred embodiment of the invention, the metering component 7 is made of a plastics material, preferably "Teflon". "Teflon" is a trademark of E. I. duPont de Nemours & Co. for a resin plastic consisting of a tetraflouroethylene polymer. This ensures an effective seal between the planar surface 10 of the metering component and the planar surface 9 of the valve component.

According to another preferred embodiment, the hose 8 is made from the same material as the metering component. Among other things this avoids movement of material between the hose and the metering component as a result of variations in temperature. It has been found that the hose remains firmly seated in the metering component, when the hose and the metering component in general are made of "Teflon" and the holes 13,14 in the metering component have a diameter slightly smaller than the outer diameter of the hose 8.

Arranged around the metering component 7 is a sleeve 17 which is arranged to press the planar surface 10 of the metering component against the planar surface 9 of the valve component. The sleeve 17 is therefore attached to the valve component 2. In accordance with one preferred embodiment the sleeve is provided in its peripheral surface with two slots 18,19 which together with pins 20,21 projecting radially outwards from the valve component 2 form a bayonet fitting.

Located in the end of the sleeve remote from the valve component 2 is a spring, for example a leaf spring 22, which is arranged to press the metering component 7 against the valve component 2. The metering component 7 is also provided with a centrally located axial hole 23. The valve component 2 is also provided with a corresponding centrally located axial hole 24. A guide means 25 is suitably arranged in the hole 24 of the valve component, the inner diameter 26 of this guide means being equal to the inner diameter 27 of the hole 23 in the metering component 7. A drive shaft 28 extends through the two holes 23,24. Thus, the drive shaft 28 is rotatably arranged relative to the valve component 2. The drive shaft is non-rotatably connected to the metering component 7 through a slot 29 located in one end of the drive shaft 28 and contacting with a pin 30 attached to the metering component and extending over one diameter of the hole 23 of the metering component. Consequently, rotation of the shaft 28 results in rotation of the metering component 7 relative to the stationary valve component 2.

FIG. 7 illustrates an assembled metering valve in side view, where solely the sleeve 17 is shown in section. For the sake of clarity the channels and hose are not shown in broken lines. As indicated, reference numeral 31 represents a portion of an outer casing of a diluting apparatus and the metering valve illustrated in FIG. 7 is preferably mounted so as to project from the outer casing 31.

When a given volume of fluid, for example blood, is to be extracted and diluted with diluting fluid, a metering component 7 having a hose 8 corresponding to said volume is mounted on the end of the drive shaft 28, whereafter the through the aforesaid bayonet fitting.

The drive shaft 28 is then rotated so as to move the metering component to the aforesaid first position of rotation. Blood is withdrawn by suction until the hose is filled. The drive shaft 28 then rotates the metering component to its second position of rotation. Diluting fluid is then pumped through the hose and into the aforesaid collecting vessel.

When desiring to extract a volume of fluid different to the aforesaid volume, the sleeve is removed by a simple manipulation of the hand and replaced with a further metering component, which in turn is secured by means of the sleeve. It will therewith be seen that the metering component can be exchanged or removed for cleaning the planar surfaces 9,10 in an extremely simple and rapid manner.

The fact that the metering component can be exchanged rapidly and simply, in combination with the fact that the metering component is inexpensive to manufacture, means that a large number of metering component of mutually different given volumes can be provided for use together with one and the same diluting apparatus, therefore enabling the apparatus to be used for different diluting processes.

So-called double-dilution processes are employed. In such cases one and the same dilution apparatus is provided with two metering valves according to the present invention. In use, a first metering valve extracts a given volume of fluid, for example blood which is diluted, whereafter the second metering valve extracts a given volume of the diluted blood, this volume being diluted in its turn.

Because the two metering components can be readily and quickly changed, it is possible to readily vary a total degree of dilution. For example, if ten metering components are available and all have mutually different extraction volume, these components can be combined two and two, so as to obtain forty-five different total degrees of dilution.

It will readily be perceived that a metering unit can be readily and quickly removed for cleaning purposes or for replacement with a unit of different volume. In addition, a large number of total degrees of dilution can be readily achieved without requiring access to a large number of expensive valves, as in the case when using known metering valves.

Thus, the drawbacks recited in the introduction are completely eliminated by means of the present invention.

The present invention is not restricted to the aforedescribed embodiment, and modifications can be made within the scope of the following claims.

I claim:

1. A metering valve for extracting a given volume of fluid from a first fluid flow and introducing the thus extracted fluid volume to a second fluid flow, comprising a stationary valve component provided with a first and a second supply channel and a first and a second discharge channel, and a metering component which is capable of being rotated in relation to the stationary component and which incorporates a metering channel of said given volume, and in which valve the valve component (2) has a planar surface (9) in which said supply channels (3,5) and said discharge channels (4,6) open out, and in which the metering component (7) incorporates a planar surface (10) which lies against the planar surface (9) of the valve component (2) and into which the two ends (11,12) of the metering channel (8) open out, said ends (11,12) being so located that in a first position of rotation of the metering component (7) relative to the valve component (2) said ends of the metering channel (8) connect the first supply channel (3) with the first discharge channel (4) of the valve component (2), and in a second position of rotation connect said second channels (5,6) of the valve component (2); said metering component and said valve component both having cylindrical bodies which are coextensive in assembly and have a common axis, and means are provided for rotating said metering component about said axis relative to said valve component; both said planar surfaces being normal to the common axis; means for removably maintaining said metering component and said valve component in coextensive assembly with said two planar surfaces in juxtaposition comprising: a sleeve with a first end and a second end and an internal surface having coextensive cylindrical portions, having a common axis, adapted to fit over both said coextensive cylindrical valve component and metering component, coupling means on said valve component and said first end of said sleeve enabling a quick disconnect coupling engagement between said sleeve and said valve component for releasably maintaining said sleeve in fixed axial relationship to said valve component, and biasing means provided within and abutting a portion of said second end of said sleeve and in engagement with and providing a bias force on said metering component maintaining said two components in assembly when said sleeve is coupled to said valve component.

2. A metering valve as defined in claim 1, wherein said coupling means comprises two slots in said first end of said sleeve and pins projecting radially outward from the exterior of said valve component cylindrical body, said slots and pins arranged to form a bayonet type coupling.

3. A metering valve as defined in claim 1, wherein said biasing means includes a leaf spring and a lid, on the end of said metering component, engaged by said spring.

4. A metering valve according to claim 1, characterized in that said metering channel (8) comprises along the whole of its length a hose which is made of a plastics material and which is inserted into axially disposed holes (13,14) in the metering component (7), said holes (13,14) opening out into said planar surface (10).

5. A metering valve according to claim 4, wherein said hose (8) and said metering component (7) are both made from a plastics material.

6. A metering valve according to claim 4, wherein a concentrically located recess (15) is provided in the metering component (7) at the opposite side from said planar surface (10), said recess (15) accommodating said hose (8); and a lid (16) sealingly closes said recess (15).

7. A metering valve as defined in claim 6, wherein said biasing means includes a leaf spring, engaging said second end of said sleeve, and said lid, said lid being engaged by said spring whereby when said sleeve is coupled to said valve component said spring is deflected to create a biasing force against said lid to maintain the lid on said metering component and to maintain said metering component in assembled juxtaposition with said valve component.

8. A metering valve according to claim 1, wherein said valve component (2) is provided with a centrally located axial hole (24); said metering component (7) is provided with a corresponding centrally located axial hole (23); and said means for rotating said metering component comprises a drive shaft (28) which extends through said holes (23,24) and is rotatable relative to the valve component (2) and means on the end of the drive shaft is non-rotatably connected to said metering component (7), so that rotation of the drive shaft (28) causes rotation of the metering component (7) relative to the valve component (2).

9. A metering valve according to claim 1, wherein at least said metering component (7) is made from a plastics material.

* * * * *